United States Patent [19]

Palacios

[11] Patent Number: 5,414,114
[45] Date of Patent: May 9, 1995

[54] METHOD FOR MAKING CONJUGATE MOIETIES CAPABLE OF CHELATING PARAMAGNETIC METALS AND DESIGNED FOR COUPLING WITH A FACTOR RESPONSIVE TO SPECIFIC CELLULAR MARKER SITES

[75] Inventor: Paul Palacios, Madrid, Spain

[73] Assignee: Bracco International B.V., Amsterdam, Netherlands

[21] Appl. No.: 975,533

[22] PCT Filed: Jul. 19, 1992

[86] PCT No.: PCT/EP92/01560

§ 371 Date: Feb. 18, 1993

§ 102(e) Date: Feb. 18, 1993

[87] PCT Pub. No.: WO93/01837

PCT Pub. Date: Feb. 4, 1993

[30] Foreign Application Priority Data

Jul. 22, 1991 [EP] European Pat. Off. ......... 91810589

[51] Int. Cl.$^6$ ............... C07C 229/04; C07C 321/14; C07D 233/04
[52] U.S. Cl. ................................ 562/556; 562/426; 562/561; 562/564; 562/565; 548/318.1; 548/319.1; 548/319.5
[58] Field of Search ............. 562/556, 561, 564, 565, 562/426; 548/318.1, 319.1, 319.5

[56] References Cited

U.S. PATENT DOCUMENTS 4,385,169 5/1983 Kato et al. ............... 528/321
5,087,616 2/1992 Myers et al. ............. 514/21

FOREIGN PATENT DOCUMENTS 0214053 11/1987 European Pat. Off.

OTHER PUBLICATIONS

Chemical Abstracts, 94(21):172633 (1981).
Medline Abstracts, AN:91248849 (1981).
Chemical Abstracts, 112(7):51816 (1986).

*Primary Examiner*—Johann Richter
*Assistant Examiner*—Michael B. Hydorn
*Attorney, Agent, or Firm*—Nixon & Vanderhye

[57] ABSTRACT

In this method, one attaches one or more chelatant molecules to a mono- or polyamino intermediate compound which is temporarily immobilized on a solid phase by a splittable bond. Thereafter, said bond is split to release the desired conjugate moiety, whereby a reactive site is generated at the splitting site. The conjugate can be coupled to a protein homing factor using said reactive site; the latter being single per chelatant molecule, undesirable cross-linking during conjugation is substantially avoided.

10 Claims, No Drawings

METHOD FOR MAKING CONJUGATE MOIETIES CAPABLE OF CHELATING PARAMAGNETIC METALS AND DESIGNED FOR COUPLING WITH A FACTOR RESPONSIVE TO SPECIFIC CELLULAR MARKER SITES

The present invention concerns a novel method for making compounds to be used in the field of administrable molecular carriers targeted for delivering paramagnetic MRI contrast enhancers to selected organs or tissues.

chelator conjugate. This conjugate was shown to achieve a binding of up to 90 mol of Gd per mol of lysine. Experimental details are however lacking in this reference. Y. MANABE et al., Biochim. & Biophys. Acta 883 (1986), 460–467, have disclosed making DTPA-linked poly(L-lysine) by reacting poly(L-lysine) of DP about 100 or so with DTPA cyclic anhydride (caDTPA), introduction therein of 2-pyridyldisulfide groups by reaction with N-succinimidyl-3-(2-pyridyldithio)-propionate (SPDP) and coupling with thiolated IgG to form a covalent thia-bonded conjugate. The reactions involved in this synthesis are summarized below.

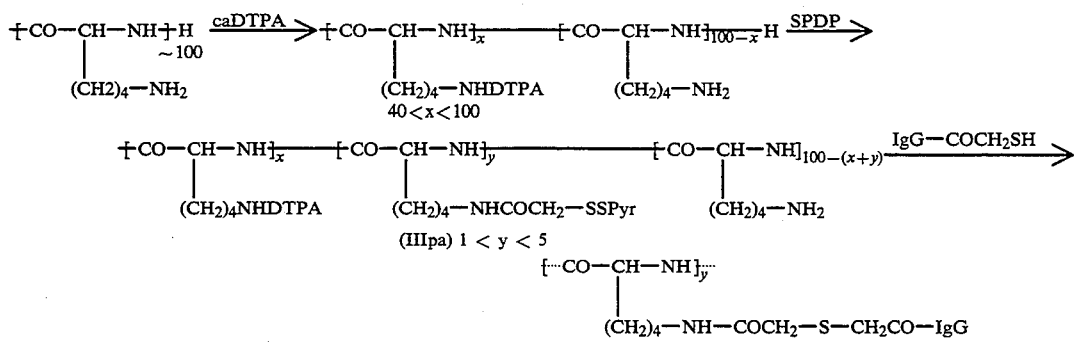

BACKGROUND OF THE INVENTION

Molecular conjugates in which a monoclonal or polyclonal antibody (cytoselective homing factor) is covalently linked to a moiety carrying aminopolycarboxylic chelatantS holding paramagnetic metal ions are known.

For instance, in W. T. ANDERSON et al., Cancer Res. 45 (1985), 2154–2158, there is disclosed the binding of up to 8 mol of DTPA per mol of antibody while retaining antibody activity and specificity. The DTPA (diethylenetriamine-pentaacetic acid) is a powerful chelatant for paramagnetic metal species including for instance Gd, Fe, Cr and Ni, which can therefore be directly targeted to specific cellular sites and aid MRI visualization by modifying proton spin relaxation ($T_1$ and/or $T_2$) and enhancing image contrast.

Also in WO-A-90/14881, there is disclosed the attachment of polyaminocarboxylic chelators to homing proteins by using bridging functional groups such as isocyanato-, isothiocyanato-, bromoacetamido-, diazo-, N-hydroxysuccinimide esters and inter-molecular or intra-molecular anhydrides.

However, the molecular ratio of chelatant to antibody was still too low for effective MRI contrast enhancement and means were developed which improved contrast enhancement efficiency. For instance, George W. and Catherine H. WU (WO-A-90/01900) have disclosed a conjugate in which a ligand such as a glycoprotein possessing exposed terminal galactose residues to be recognized by unique receptors at the surface of given types of cells is coupled to a chelating agent, e.g. DTPA or DOTA (1,4,7,10-tetrazacyclododecane-$N_4$-tetraacetic acid), capable of binding a paramagnetic species and form a stable and non-toxic complex. A selective protein was asialoorosomucoid (AsOR), and DTPA was coupled thereto by undisclosed means in order to eventually achieve a molar ratio of chelated Gd to AsOR in the range of 5:1 to 15:1 In another embodiment, polylysine (PL) was modified by reacting with the lactose terminals of the desialylated glycoprotein and thereafter with DTPA to yield an asia-PL- A similar technique is disclosed by P. Shreve et al. in Magnetic Resonance in Medicine 3 (1986), 336–340.

P. F. Sieving et al., Bioconjugate Chem. 1 (1990), 65–71, have disclosed the binding of polyaminocarboxylic chelatants to the side-chain terminal $—NH_2$'s of polylysine by means of a technique involving mixed anhydrides. The latter resulted from treating the chelates (e.g. DTPA and DOTA) in the form of their salts with organic amines such as triethylamine or tetramethylguanidine with isobutyl chloroformate (IBCF). The chelatant bearing polylysine was thereafter coupled to human serum albumin (HSA) as follows: Residual unreacted amine side groups of the polylysine were derivatized with succinimidyl-4-(N-maleinimidomethyl)-cyclohexane-1-carboxylate (SMCC) to provide maleinimido activated residues, while some free amino groups of the HSA were activated with 2-iminothiolane to provide at least one reactive alkylthiol group. Final coupling resulted from the addition of said thiol of the HSA to the double bond of the maleinimido terminals of the chelatant carrying polylysine. It was estimated that the conjugate obtained contained an average of about 70 chelating sites per targeting protein.

The foregoing techniques have however the drawback that each step involves careful chromatographic purification of the intermediate products, which operations require tedious manipulations and give low yields. In the present invention, there is provided an improved method to prepare a conjugate moiety of formula III capable of complexing paramagnetic metal ions which can be coupled to protein homing factors specifically responsive to selected cellular marker sites, thus furnishing administable compounds capable of selectively carrying and delivering high ratios of paramagnetic MRI contrast enhancing species to predetermined areas, both in vivo and in tissue cultures.

DESCRIPTION OF THE INVENTION

According to one aspect of the present invention, there is provided a method for preparing a conjugate moiety of formula III to be used for coupling with targeting factors specifically responsive and/or binding to bioactive cellular marker sites of living tissues in order to provide administratable targeted conjugates capable of carrying paramagnetic MRI contrast enhancers species to be selectively delivered to organs or tissues of interest. The conjugate moiety of formula III carries at least one polyalkyleneaminopolycarboxylic acid chelatant group and has the formula:

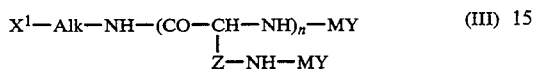  (III)

wherein $X^1$ is a —CHO or —SH group; Alk is a $C_1$ to $C_4$ alkylene, optionally interrupted by a —S— bond; Z is a $C_1$ to $C_4$ alkylene, optionally interrupted by a —COO— bond; at least one Y represents a polyalkyleneaminopolycarboxylic acid chelatant group (the other Y, if any, begin H) either in its free acid form or as a complex with a paramagnetic ion; n is an integer from 0 to about 100; and M represents a link between —NH and Y, the link being either an amido bond involving a —CO of Y and said —NH of formula III, or an organic bridging substituent formed from a group selected from the group consisting of benzene diazonium, haloacetamido-phenyl, haloacetamidobenzyl, isocyanatophenyl, isothiocyanatophenyl and azoimidate, connecting to an alkylene carbon of Y. The method comprises the step of breaking the —XX— bond of a compound of the formula IV:

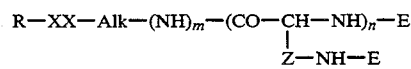

wherein R is an immobilizing solid phase to which the remainder of the molecule of formula IV is linked covalently, either directly or via a linker grafted on the surface of the solid phase, X is —S— or —CHOH—, Alk, Z and n are as defined above, E is H or MY, wherein MY is as defined above, m is 0 when E is H and m is 1 when E is MY, the solid phase being recoverable after breaking the —XX— bond and being reusable afterwards in another preparative cycle, to form the moiety (III).

The method of the present invention is based on using an immobilizing phase for binding the starting materials and, subsequently, the successive intermediates as the synthesis progresses. In the last step, the desired product is released from the immobilizing phase by a splitting reaction which simultaneously generates a reactive end function for coupling with the targeting factor. The advantage of using an immobilizing phase particularly proves itself in the separation of the intermediates since this can be effected by simple filtration or centrifugation. Another advantage of the present method is that the splitting step will release only one terminal activated group per molecule, whereas in the past methods the corresponding intermediates often carried several reactive ends which lead to crosslinking upon coupling with the homing factor. One further advantage particularly reflects in the carrying out of step (Ia) when the selected acylating compound is an internal anhydride with more than one iminodiacetic ring, whereby such double functionality may lead to cross-linking. When using compounds of formula I immobilized on a solid phase, cross-linking during acylation with polyfunctional anhydrides is impeded due to steric reasons.

In the present method, the immobilizing solid phase schematized by the symbol R, can be a polymeric resin with residual reactive groups on the surface or mineral particles (glasses or ceramics) provided with grafted substituents capable of forming the starting component I in a procedure requiring one or more steps. For instance, resins like polyacrylics, polystyrene, polyamides, polyesters, polyimides, polyolefins, etc. are convenient. In the field of mineral particles, powders or beads of ceramics like alumina, silica, rutile or porous glass are convenient. The mineral particles, preferably porous glass beads, can be made reactive by silanation with trialkoxysilanes provided with reactive end groups such as isocyanato, amino, amido, substituted oxycarbonyl, hydroxy, thiol and the like. In a preferred embodiment, the beads are silanated with a thioalkyl-silane (see H. WEETALL, Covalent Coupling Methods for Inorganic Support Materials, in Meth. Enzym. 44 (1976), 134) and the product is reacted with cysteamine to provide an immobilized intermediate amine containing a splittable disulfide bond (—XX—=$S_2$), (see L. FIELD et al., J.A.C.S. 83 (1961), 4414). Otherwise, thiolated resins, e.g. Thiosepharose, are also convenient starting materials.

In some embodiments, the immobilized amine can thereafter be used as initiator in the telechelic polymerisation of aminoacid N-carbonyl anhydrides (NCA's) to provide the starting compound I in which n≠0; details on such reactions are given hereafter. It should be noted that polyolefins derivatized with haloalkyls can be sulfidated with thiourea in the presence of bis(aminopropyl)amine (see WARDELL, The Chemistry of Thiol Groups, Part I, Ed. Patai, Wiley (1974) New York) to also provide suitable starting materials. Also resins available with thiomethyl group (Merrifield Resins) can be provided with amino-alkyldithia-substituents by the same reaction with cysteamine (HS($CH_2$)$_2$—SH), with or without the intermediate action of dithiopyridine (H. YAHIMA et al., J. Am. Chem. Soc.63 (1941), 2263.

The reactions in which one starts with a haloalkylated resin are summarized hereafter:

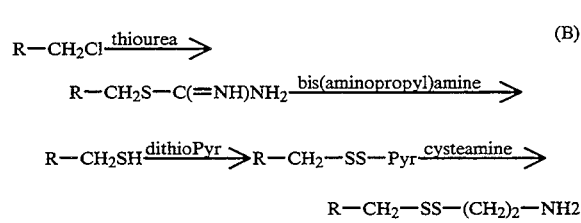  (B)

In other embodiments of the present invention, the solid phases were silanated with epoxypropyl-silane to provide oxirane grafted materials, this function being actually already present on some grades of commercial polyacrylamide resins, viz. the Eupergit resins from SIGMA Chemicals. Oxirane derivatized immobilizing phases were used to make vicdiol carrying intermediates, i.e. compounds I where the —XX— is —CHOH—CHOH— by the following reactions:

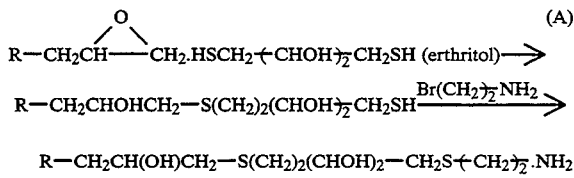

(A)

The terminal amino group of compounds B and A can then used for direct binding with a chelatant molecule, either in the free state or already in under complex form with paramagnetic metal ions, according to the means known in the art, e.g. mentioned in the introduction, especially in Liu YUANFANG et al., Pure & Applied Chem. 63 (1991), 427–463. One embodiment means is to acylate the amine by using an anhydride of the chelatant anhydride (an intramolecular anhydride, i.e. provided with at least one iminodiacetic anhydride ring, or an intermolecular anhydride involving two molecules of the same or different kinds) of the selected polyalkyleneamino-polycarboxylic chelatant. A preferred reagent for forming heterogeneous intermolecular anhydrides is i.butylchloroformate (see Bioconjugate Chem. 1, (1990), 65–71.

Then, step (2) of the method of the invention is undertaken to split the chelatant from the immobilizing phase while simultaneously generating thereon a reactive group for attaching to a protein targeting factor, the latter requiring or not requiring to be activated before coupling.

In the case of compounds of type A above, the splitting can be effected by selective oxidation or peroxidation by usual means of the vic-diol bond whereby a reactive aldehyde of formula $OHC-CH_2SCH_2-CH_2NH-MY$ will be released in which M and Y have the meaning defined above.

In the case of compounds of type B the splitting is effected at the disulfide bond by usual means, i.e. in the presence of mercaptans like thioethanol or dithiothreitol. In this case, the released chelatant molecule, of typical formula $HS-(CH_2)_2-NH-MY$, can be used for coupling with sulfide activated protein homing factors according to usual means (cf. the techniques disclosed in the references cited in the introduction). After splitting, the immobilizing phase can be recovered, for instance by filtration or centrifugation and reused in another cycle which is economically attractive. In the case of the immobilizing phase being released with an aldehyde-sulfide substituent, this can be used in other syntheses or regenerated by conventional means for reuse in another cycle of the present method.

According to one further particularly interesting aspect of the present invention, the immobilized amines of formulae A or B can be used as initiators for the telechelic polymerisation of aminoacid anhydrides (NCA's) (see E. J. GOETHALS, Telechelic Polymers, Synthesis and Applications, CRC Press (1989), New York) to provide polyaminoacids, i.e. compounds with a polymeric backbone having a plurality of sites for attaching chelatant molecules. By this technique, one will advantageously increase the number of chelated paramagnetic ions per targeting molecule after coupling. In some embodiments of the invention, the compound B was used for polymerizing the NCA's of some γ-protected derivatives of L-glutamic acid or the corresponding β-derivatives of aspartic acid, the protective groups being selected from benzyl, phenacyl, piperonyl and p-methoxyphenacyl.

The esters themselves were prepared according to Van HEESWIJK, Synthesis. (1982),744 and the NCA's were obtained by the reaction with phosgene (gaseous or solid triphosgene). After polymerisation, the polyaminoacids with amine initiator head attached thereto were deprotected by usual means, e.g. with HBr or trifluoroacetic acid (TFA), and the free carboxylic function amidated with ethylenediamine (or any alkylene diamine) to provide primary amine terminated side groups. The chelatant molecules were attached to said amine terminal side groups as explained above in the case of compounds A or B, i.e. either by acylation or directly using a reactive connecting bridge from one of the alkylene carbons of the polyalkyleneamine-polycarboxylic chelatant molecule. Then, the XX bond was split under conditions similar to that already mentioned before so as to release the free activated chelatant polymer to be thereafter coupled (with the carboxylic groups free or complexed with a paramagnetic metal) to a targeting homing factor.

Similar reactions were carried out using the NCA of L-lysine, the ε-$NH_2$ groups being protected with either a fluorenyloxycarbonyl (PFL) group or by benzyloxycarbonyl (PBL). Deprotection after polymerisation was afforded by using piperidine in DMF or mixtures of TFA and mesylic acid in dioxane (see the Examples below).

The telechelic polyaminoacids obtained as described above are therefore provided with a plurality of amine terminated side groups to which chelatant molecules can thereafter be bound by the same methods already described hereinbefore. For instance, immobilized polylysine obtained after polymerisation of L-lysine-NCA initiated by immobilized compound A was reacted with caDTPA to provide a polyaminoacid of DP approximately 50 to 110 in which a significant proportion (up to 60–80%) of the side arms were equipped with the chelatant molecules. Then, after release by oxidation, as already explained heretofore, the resulting polychelatant comprising a —CHO head group could be used for coupling with a protein homing factor, no need to activate the protein before coupling being necessary; this is obviously a strong advantage of the invention compared to the techniques of the prior art. The proteins which can be used as homing factors are very numerous and include for instance monoclonal and polyclonal antibodies, human serum albumin (HSA), specific an non-specific Ig's, α-2-macroglobulin, interleukin, epidermal growth factor (EGF), platelet derived growths factors and, in general proteins or glycoproteins recognizing specific cellular marker sites.

The Examples which follows illustrate the invention in more detail. In this section, the symbol AcOH defines acetic acid groups.

EXAMPLES

Benzyl glutamate-NCA was prepared according to H. BLOCK, "Ring Opening Polymerization" 2 (1969), 23, K. C. FRISH & S. L. REEGEN Eds., MARCEL DEKKER, New York.

Gamma-phenacyl glutamate-NCA was obtained by bubbling phosgene in a suspension of 8.6 g of glutamic ester in 250 ml of THF. When dissolution was complete, the solution was flushed with nitrogen; then it was evaporated and the residual solid was crystallized from ethyl acetate and hexane; colorless crystals were obtained.

The NCA of γ-piperonyl glutamate was obtained by treating a suspension of 1 g of the ester in 20 ml of dioxane with 350 mg of solid triphosgene (Janssen) and, thereafter, further agitating 90 min at 60° C. If necessary, full dissolution is brought about by adding very small further portions of triphosgene. The solution was poured into 400 ml of hexane and the whole was left standing overnight at −20° C., whereby crystals formed. These were dissolved in a small amount of ethyl acetate, the solution was bleached with carbon at 40° C. and precipitated with hexane. White crystals were obtained after repeated purifications.

Example 1

A) Preparation of carrier with grafted primary amines via a vic diol spacer (amino-diol-derivatized carrier.

Five g of Eupergit-C beads (a polyacrylamide resin with glycidyl groups grafted thereon—a product of SIGMA) were suspended in 100 ml of 0.1M phosphate (1 mM EDTA) buffer pH 6.0 and 1 g (6.5 mmol) of dithioerythritol (DTE), a large excess thereof, was added under stirring. The heterogeneous mixture was stirred for 2 days at room temperature, after which the beads were drained and washed with the same phosphate buffer. Analysis was performed by taking an aliquot of ∼50 mg and stirring for 1 h at room temperature with 10 ml of a 10 mM solution of 2,2′-dithiodipyridine in DMF. The beads were drained, washed with DMF, then with CH2Cl2, resuspended in 5 ml of DMF, and the —SS— bond split with one drop of mercaptoethanol (EtSH); after stirring for 30 min, the beads were separated by filtration and the amount of 2-thiopyridone determined in the filtrate by absorbance at 343 nm (ε=8080) according to M. C. Millot et al., J. Chromatography 354 (1986) 155.

The beads (main portion) were suspended in 100 ml of 0.5M Tris-HCl (0.5 mM EDTA) buffer, pH 8.5 and a quantity of 2-bromoethylamine hydrobromide (calculated from the results of the foregoing analysis) to make a mole ratio bromoamine/thiol of 50, this being according to K. Okazaki et al., Anal. Biochem. 149 (1985) 516. After stirring for 2 days at room temperature, the beads were drained, washed with the same buffer, then with H2O and dried in vacuo.

Analysis of the free amino groups was effected according to C. C. Y. Lee and G. M. Loudon, Anal. Biochem. 94 (1979) 60 and an average value (after several runs) was about 50 μmol —NH2/g of dry beads. The reactions are (R=carrier):

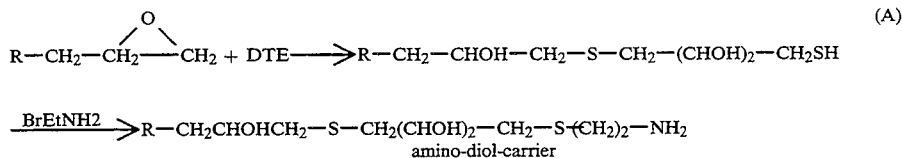

B) Preparation of aldehyde-derivatized DTPA

One g (2.8 mmol) of DTPA bis anhydride (caDTPA) (from Pierce Chemicals) was dissolved in 100 ml of dry DMF, 10 mmol of triethylamine (TEA) were added and thereafter 2 g, (0.1 mmol) of the beads derivatized as under Example 1 above. The suspension was stirred for 24 h at room temperature after which they were drained, washed with DMF and resuspended in 100 ml of DMF containing 1 g (2.8 mmol) of caDTPA and 10 mmol of TEA. After 24 h of agitation the beads were again drained and washed with successively DMF, dimethylsulfoxide (DMSO), and slightly acidified water (HCl). The beads were suspended in 10 ml of 0.1M phosphate (0.01M NaIO4) buffer pH 7 and stirred for 30 min in the dark, then the beads were drained and washed with the same buffer. The filtrate and washing fractions were pooled.

The pooled filtrate and washing fractions were acidified to pH 2 (with HCl) and concentrated to abut 2 ml in a Rotavapor. Then the residue was passed over an ion-exchange resin (Dowex 1X8, acetate form, 20–50 dry mesh) in a 20×1 cm column. The elution rate was 2 ml/min using a constant acetic acid gradient (pH=3). Aliquots from the successive fractions (2 ml) were analysed for aldehyde by the method of J. Bartos et al. Pure Appl. Chem. 51 (1979) 1803 measuring the fluorescence generated after treatment with cyclohexanone and ammonium carbonate. On a total of 10 fractions, the 6th and 7th contained the majority of the aldehyde-derivatized DTPA. The fractions giving a positive aldehyde signal were pooled and lyophilized. The product was analysed by NMR and for aldehyde according to Bartos (ibid).

The weight of dried product seemed to indicated a yield of release from the carried of abut 100% and it is likely that the obtained DTPA is aldehyde-monosubstituted since steric hindrance by the matrix network would probably inhibit dual DTPA linking to the solid phase. However measurement of aldehyde seems to indicate that only half of theoretical substitution has occurred. The discrepancy may tentatively by explained by some degree of overoxidation during release with possible partial conversion to carboxylic groups.

The reactions are schematized below (A is the amino-diol-carrier, see Part A above):

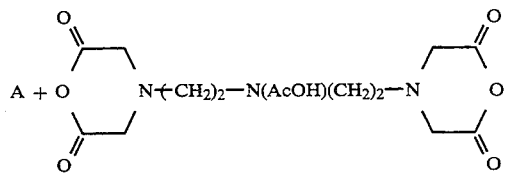

-continued

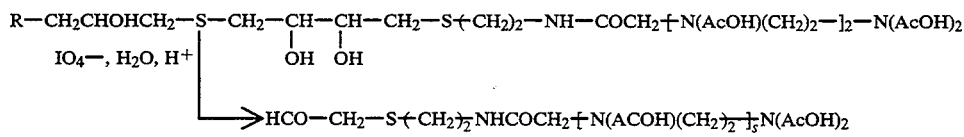

Example 2

Preparation of DTPA-grafted poly (L-lysine) provided with an aldehyde heading group.

a) The polymerization of the N-carboxyanhydride (NCA) of alkyloxy carbonyl-protected lysine was initiated by the amine group of the amino-diol derivatized Eupergit carrier disclosed under Example 1(A). The protected lysine monomers i.e. ε-benzyloxycarbonyl-L-lysine (BL) and ε-fluorenyl-methyl-oxycarbonyl-L-lysine (FL) were purchased from Bachem (Switzerland).

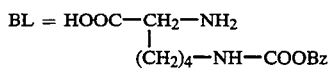

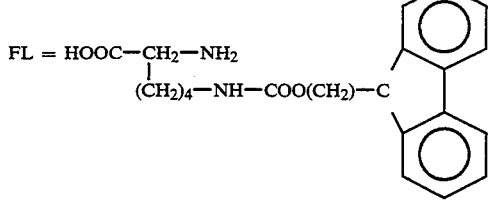

The corresponding NCA's were prepared according to W. H. Daly et al. Tetrahedron Letters 46 (1988) 5859 by reaction with solid triphosgene in THF.

b) Ten mmol of the BL- or FL-NCA were agitated for three days at room temperature with 2 g (0.1 mmol) of the amino-diol derivatized carrier prepared under Example 1 hereabove in 40 ml of dioxane (BL-NCA) or DMF (FL-NCA) using a Rotavapor apparatus. The beads were drained and washed with successively dioxane or DMF, then CH2Cl2; finally they were dried in vacuo and weighed. The amount of polymer obtained was determined by the carrier weight increase. Yield 90% (BL), 40% (FL).

The methyl fluorenyl group of the poly-(ε-fluorenyl-methyloxycarbonyl-L-lysine) (PFL)-derivatized substrate (5 g) was removed by stirring for 30 min in 50 ml of a 20% solution of piperidine in DMF. Then the beads were washed repeatedly with DMF, with CH2Cl2 and dried in vacuo. The yield of deprotection was near 100%. Corresponding poly (ε-benzyloxycarbonyl-L-lysine) (PBL)-derivatized beads (1 g) was deprotected by stirring for 60 min in 50 ml of a 33:67 mixture of HBr/AcOH, then repeatedly washing with H2O, EtOH and CH2 Cl2 and dried in vacuo. In this case, a ninhydrine test showed the deprotection to be incomplete and further operations were carried out using preferably the derivatized carried resulting from the near 100% deprotection by removal of FL.

c) One g of the deprotected polylysine (PL)-derivatized Eupergit was suspended in 20 ml of DMSO containing 1 g of caDTPA for 24 h at room temperature. Then one more g of caDTPA was added and the mixture was further stirred for 24 h. This was repeated until no left free amino groups were present as ascertained with ninhydrine (no color). Then beads were again separated and washed free of DMSO.

d) The DTPA-grafted PL- carrier was suspended in 20 ml of 0.1M phosphate (0.01M sodium periodate) buffer pH 7.0 and stirred for 30 min in the dark. The carrier was drained and washed with the same buffer. The filtrate and washing were reunited and purified by dialysis against water (membrane MW cut-off 5000). The residue was freeze-dried to give about 50% yield of polymer. Analysis of the aldehyde groups showed that abut 15% of the polymer chains were provided with a reactive —CHO group. It is postulated that this yield may be increased by using milder oxidation conditions for release of the carrier. The reactions are illustrated by the scheme on the next page (only the FL embodiment is represented).

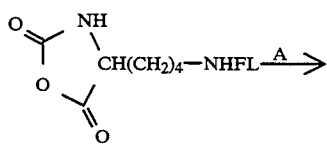

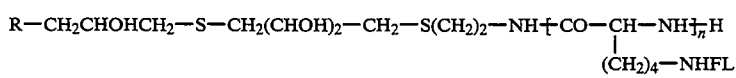

base ↓

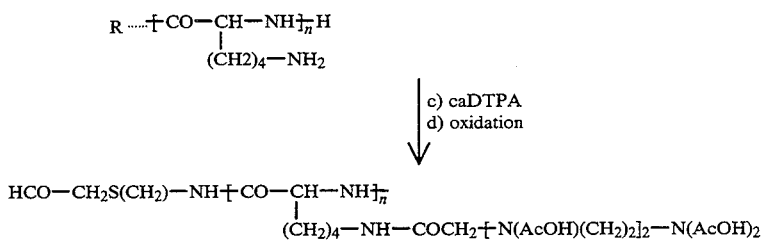

Example 3

Preparation of DTPA-grafted poly-(L-lysine) provided with a thiol leading group a) Grafting of propane-thiol To a suspension of 4.24 g glass chips (controlled pore glass CPG-10-1000 from Fluka AG) washed with water and hot nitric acid in 50 ml of phosphate buffer (0.1M, pH 7, 1 mM EDTA) were added 4.24 ml of a stirred (2 h) solution of 3.7 ml of 3-mercaptopropyl trimethoxysilane (3.7 ml) in 20 ml of 1:1 acetate buffer/ethanol (pH 4). The glass chips were stirred overnight, washed with 1:1 water/ethanol and resuspended in ethanol (20 ml) containing 1.2 g (10 mmol) of dithiodipyridine. After two hours, the glass chips were removed and washed with ethanol then dried. Yield 7 µmol of thiol groups/g of glass. A similar technique was applied for thiolating silica particles (Aerosil-A300), alumina and titanium dioxide (P25).

b) grafting of initiator

Thiolated glass chips (1.75 g) were suspended in 20 ml of DMF and a large excess of cysteamine (250 mg, 3 mmol) was added. The suspension was stirred overnight and the glass chips were separated and washed with successively DMF, chloroform, ethanol, very dilute aqueous acid, NaHCO3 and finally DMF.

c) Polymerization of ε-protected lysine

The procedure was similar to that disclosed in Example 2. Ten mmol of FL-NCA were agitated for 48 h at room temperature with 1 mmol of the amine-substituted carrier prepared as indicated above under a in 50 ml of DMF freshly distilled to eliminate traces of amine impurities after which they were separated and washed with DMF and then CH2Cl2. Deprotection was effected also as described in Example 2 using piperidine in DMF.

d) Grafting of ca DTPA on the deprotected ε-NH2 groups

The procedure was exactly that disclosed in Example 2 using an excess of caDTPA and allowing the reaction to proceed until substantial exhaustion of the free NH2 groups is accomplished. Then the glass chips were separated and washed free of DMSO with dioxane and CH2Cl2.

e) Release of the DTPA-grafted polymer The glass chips with immobilized DTPA-derivatized polylysine were suspended in 20 ml of phosphate buffer (0.1M, pH 7, 1 mM EDTA) and 100 mg of dithiothreitol were added. After stirring overnight, the glass chips were removed by filtration and washed with the same buffer; the filtrate provided after evaporation in vacuo the product in the form of the thiol-terminated polymer (yield 76%).

The reactions are schematized in the next page, where R represents the immobilizing glass carrier. The surface of the carrier is provided with a density of hydroxy groups (of adsorbed moisture or silica) which enable condensation with the silane derivative.

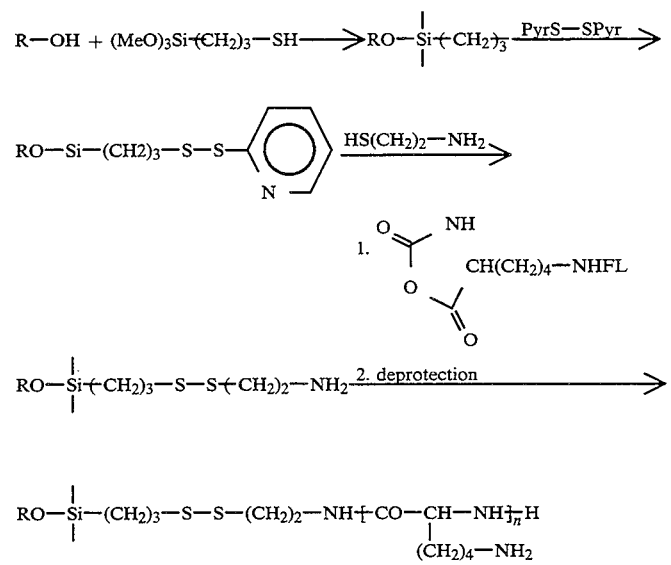

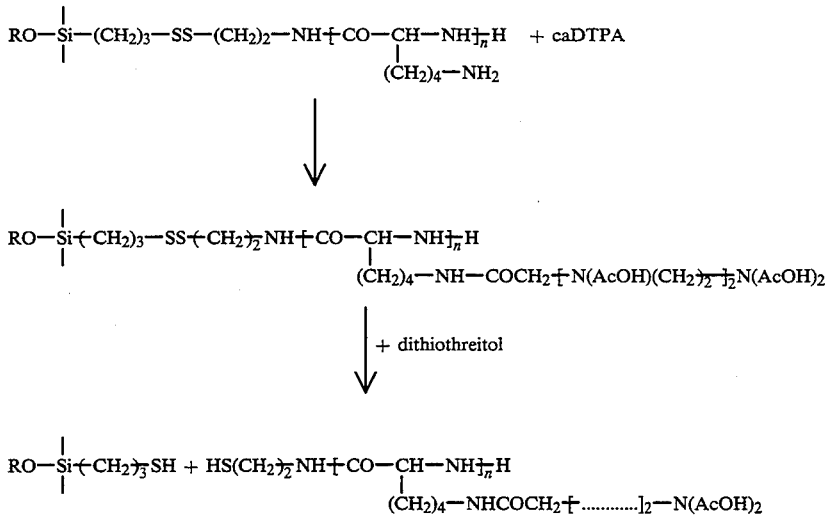

Example 4

The use of DTPA-grafted polymers with aldehyde functionality as the homing moiety in a conjugate vector for carrying MRI contrast enhancers to selected areas.

A quantity of non-specific human immunoglobulin nIg (Sigma) 0.9 mg (about 6 nmol) was dissolved in 0.9 ml of a 1% acetate buffer pH 5.5; then there were added an amount of the aldehyde terminated polymer (see Example 2) and an amount of sodium cyanoborohydride dissolved in 20 μl of water, said amounts being such as to provide a mole ratio of antibody/aldehyde/reducing agent of 1/10/5. After stirring for 8 h at room temperature, there was added a new portion of cyanoborohydride and stirring was continued for 16 h. The mixture was thereafter diafiltered through a 100'000 MW cut-off membrane with 10 mM (0.15M NaCl) phosphate buffer pH 7.2 (PBS) in order to remove the excess of reducing agent and unreacted polymer.

Then the solution (0.5 ml) was chromatographed on a gel-permeation column available from Beckman and equilibrated with PBS. Two peaks were obtained: a first fraction containing nIg and a second fraction containing the desired nIg coupled with the polymer. This latter fraction was concentrated by ultrafiltration using a 10'000 MW cut-off membrane to obtain a product to be directly used to complex paramagnetic ions and thereafter be injected for in vivo MRI experiments. This material was capable of complexing from about 50 to about 100 $Gd^{+3}$ per mole of Ig. In other experiments, the nIg was replaced by other targeting factors and similar results were observed.

Example 5

The use of DTPA-grafted polymers with thiol functionality as a homing moiety in an injectable conjugate for selectively carrying MRI contrast enhancers to selected areas in vivo.

To 0.9 mg of nIg (or anti-mouse CEA 35 from the Institute of Biochemistry, Lausanne) in 0.9 ml of PBS buffer were added 60 nmol of N-succinimidyl-4-(N-maleinimido) butyrate (SMBU) from Sigma dissolved in 50 μl of DMF. After 1 h rest at room temperature, the solution was diafiltered through a 10'000 MW cut-off membrane with PBS in order to remove the excess of SMBU.

Then there was added 16 nmol of DTPA-polylysine with SH-functionality (see Example 3) in 40 μl of PBS. After 2 h rest at room temperature, the conjugate was subjected to purification (as under Example 4 above) to provide an injectable solution to be used for in vivo MRI contrast enhancement tests.

Example 6

Beads of a macro-crosslinked polystyrene resin (from Polysciences) were etched for 48 hrs. in TFA, then they were washed with, successively, DMF, dioxane and MeOH. The beads, 15.5 g, were suspended in 80 ml of $CHCl_3$ and a mixture of stannic bromide (1,8 ml, 13.7 mmol) and bromomethyl-methyl-ether (18.6 ml, 228 mmol) were added dropwise to the suspension agitated at 0° C. under nitrogen. After standing a while, the resin was washed with, successively, dioxane-HCl 3N (3:1), dioxane, methanol and chloroform. The dried beads were suspended in 90 ml of DMF and the suspension was heated to 100° C. (reflux condenser) under $N_2$, after which a solution of 2.1 g (27.9 mmol) of thiourea in very little DMF was added and the mixture was left at 100° C. overnight. After washing with DMF the substrate was again suspended in 90 ml of DMF containing 3.6 g of bis(3-aminopropylamine) and heated overnight at 100° C. under nitrogen. Then the beads were washed with, successively, DMF, dioxane and chloroform, then they were dried under vacuum.

The resin (15.5 g, 512 μeq of —SH) was suspended in 140 ml of 50% aqueous ethanol containing 0.8 g of cysteamine (10.4 mmol), and there was added thereto 3% $H_2O_2$ until no further reduction of $I_2/KI$ solution by an aliquot of the mixture is observed. After agitating overnight, the beads were washed with aqueous ethanol, then with water. They were further extracted overnight in a Soxhlet apparatus with 1:1 MeOH/chloroform, then they were dried under vacuum.

A portion of 8 g of the aminated disulfide grafted solid phase was suspended in 30 ml of dioxane and a solution of 5.2 g of the N-carboxy anhydride of γ-benzyl glutamate (BG-NCA) in 20 ml of dioxane was added. After stirring for 3 days, the resin was drained and washed with, successively, dioxane, MeOH and CHCl₃. A portion of 4 g of the above beads with immobilized polyglutamate suspended in 35 ml of benzene was put in 40 ml of benzene saturated with HBr and agitated for 1 hr, HBr bubbling being pursued. Then the introduction of gas was stopped and agitation was continued overnight, after which the beads were collected and rinsed as usual, the last solvent being dichloromethane. The free carboxyl functions of the immobilized polyglutamic were thereafter amidated with ethylene diamine under usual conditions and the reaction of the free amine terminated side chains with caDTPA was brought about as disclosed in the previous examples. Finally, the beads were suspended in DMF and the thiol activated polychelator molecule was released by adding 3% (based on the volume of solvent) of thioethanol. The yield of release exceeded 50% after 72 hrs. at 120° C. The final product was obtained after separating the solid phase by filtration and evaporating the filtrate under reduced pressure. The separated solid phase was reusable in another In the embodiments of this invention, there were used mainly polyalkyleneaminopolycarboxylic chelatants of general linear backbone exemplified by the structures of EDTA or DTPA. Naturally, chelatants with other structures can also be employed, viz. starlike compounds such as nitrilotriacetic acid and the triethyleneaminohexaacetic homolog as well as the macrocyclic chelatants like cyclotetrazadodecanes tetraacetic acid (DOTA) and other similar structures (see for instance DE-A-3401052). Derivatives of the polyalkyleneaminopolycarboxylic acids with one or more of the carboxylic groups being replaced by hydroxy, alkoxy or amide groups are also usable in the present method; a typical example of chelatant with an alkoxy—side group is the DTPA analog of which on of the terminal carboxy has been replaced by a benzyloxy group (BOPTA).

I claim:

1. A method for preparing a conjugate moiety of formula (III) to be used for coupling with targeting factors specifically responsive and/or binding to bioactive cellular marker sites of living tissues in order to provide administrable targeted conjugates capable of carrying paramagnetic MRI contrast enhancer species to be selectively delivered to organs or tissues of interest, the said conjugate moiety III carrying at least one polyalkyleneaminopolycarboxylic acid chelatant group and having the formula:

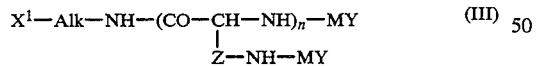

wherein $X^1$ is a —CHO or —SH group;

Alk is a $C_1$ to $C_4$ alkylene, optionally interrupted by a —S— bond;

Z is a $C_1$ to $C_4$ alkylene, optionally interrupted by a —COO— bond;

Y represents H or a polyalkyleneaminopolycarboxylic acid chelatant group either in its free acid form or as a complex with a paramagnetic ion, at least one of Y being a said polyalkyleneaminopolycarboxylic acid chelatant group either in its free acid form or as a complex with a paramagnetic ion;

n is an integer from 0 to about 100; and

M represents a link between —NH and Y, said link being either an amido bond involving a —CO of Y and said —NH of formula (III), or an organic bridging substituent formed from a group selected from the group consisting of benzene diazonium, haloacetamido-phenyl, haloacetamidobenzyl, isocyanatophenyl, isothiocyanatophenyl and azoimidate, connecting said —NH to an alkylene carbon of Y;

said method comprising the step of breaking the —XX— bond of a compound of the formula (IV):

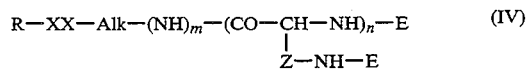

wherein R is an immobilizing solid phase to which the remainder of the molecule of formula (IV) is linked covalently, either directly or via a linker grafted on the surface of said solid phase, X is —S— or —CHOH—, Alk, Z and n are as defined above, E is H or MY, wherein MY is as defined above, m is 0 when E is H and m is 1 when E is MY, said breaking of said —XX— bond being effected by hydrolysis when X is S and by oxidation when X is CHOH said solid phase being recoverable after breaking said —XX— bond and being reusable afterwards in another preparative cycle, to form the moiety (III).

2. The method of claim 1, in which said derivative of a polyalkylene aminopolycarboxylic acid chelatanty has the structure of an intermolecular anhydride where at least two gem-acetoxy groups are in the form of an iminodiacetic anhydride ring, with the formula:

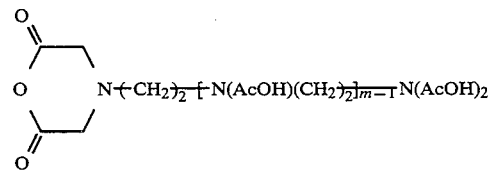

wherein m is 2.

3. The method of claim 1, in which the solid phase R comprises porous or non-porous organic material particles or beads.

4. The method of claim 3, in which said organic phase is a polymeric resin selected from the group consisting of polystyrene, sepharose, agarose, thiosepharose, polyacrylate, polyacrylamides, polyesters, polyamides and polyimides, and said mineral phase is a glass, metal oxide or ceramic selected from the group consisting of porous and non-porous filtrating beads or powders of glass, silica, alumina, $ZrO_2$ and $TiO_2$.

5. The method of claim 2, in which in formula (III) $X^1$ is —SH, X is —S—, Alk is ethylene, Z is tetramethylene, and n is between about 50 and 110.

6. The method of claim 2, in which formula (III) $X^1$ is —SH, X is —S—, Alk is ethylene, $Z=-(CH_2)-COO(CH_2)_2$ and n is between 50 and 110.

7. The method of claim 5, in which breaking the —XX— bond is effected by hydrolysis.

8. The method of claim 6, in which formula (III) $X^1$ is —CHO, X is CHOH—, Alk is —$CH_2S(CH_2)_2$, Z is $(CH_2)_4$ and n is between 50 and 110.

9. The method of claim 2, in which formula (III) $X^1$ is —CHO, $X=-CHOH-$, $Alk=-CH_2S(CH_2)_2$, $Z=(CH_2)_4$ and n is zero.

10. The method of claim 8, in which breaking the —XX— is effected by oxidation.

* * * * *